United States Patent
Ajiki et al.

(10) Patent No.: US 9,457,185 B2
(45) Date of Patent: Oct. 4, 2016

(54) MUSCLE SUPPORTER AND MUSCLE SUPPORT METHOD

(71) Applicant: Panasonic Intellectual Property Management Co., Ltd., Osaka (JP)

(72) Inventors: Kaori Ajiki, Osaka (JP); Sachiko Takeshita, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 16 days.

(21) Appl. No.: 14/606,212

(22) Filed: Jan. 27, 2015

(65) Prior Publication Data

US 2015/0224309 A1 Aug. 13, 2015

(30) Foreign Application Priority Data

Feb. 7, 2014 (JP) .................................. 2014-022413

(51) Int. Cl.
- *A61N 1/36* (2006.01)
- *A61N 1/04* (2006.01)
- *A61N 1/32* (2006.01)

(52) U.S. Cl.
CPC ......... *A61N 1/36003* (2013.01); *A61N 1/0452* (2013.01); *A61N 1/0484* (2013.01); *A61N 1/36014* (2013.01); *A61N 1/321* (2013.01)

(58) Field of Classification Search
CPC ........... A61N 1/36003; A61N 1/0452; A61N 1/0484
See application file for complete search history.

(56) References Cited

U.S. PATENT DOCUMENTS

| | | |
|---|---|---|
| 2003/0074029 A1 | 4/2003 | Deno et al. |
| 2006/0074458 A1 | 4/2006 | Imran |
| 2007/0257256 A1 | 11/2007 | Kugler |
| 2009/0058274 A1 | 3/2009 | Yokoyama et al. |
| 2010/0305484 A1 | 12/2010 | Grollier et al. |
| 2011/0071595 A1 | 3/2011 | Muccio |
| 2012/0302821 A1 | 11/2012 | Burnett |
| 2013/0123568 A1 | 5/2013 | Hamilton et al. |
| 2014/0049137 A1 | 2/2014 | Ando et al. |

FOREIGN PATENT DOCUMENTS

| | | |
|---|---|---|
| CA | 2858824 | 6/2013 |
| JP | 4-312472 | 11/1992 |

(Continued)

OTHER PUBLICATIONS

The Extended European Search Report dated Aug. 28, 2015 for the related European Patent Application No. 15152420.4.

(Continued)

*Primary Examiner* — Joseph Dietrich
(74) *Attorney, Agent, or Firm* — Greenblum & Bernstein, P.L.C.

(57) ABSTRACT

A muscle supporter includes a sheet member that is to be closely attached to skin covering a muscle, a muscle strength condition detector, a muscle contraction timing detector, and a muscle assist movement provider. The muscle strength condition detector disposed on the sheet member detects information related to muscle strength condition of the muscle. The muscle contraction timing detector disposed on the sheet member, in operation, detects a muscle contraction timing of the muscle. The muscle assist movement provider disposed on the sheet member, in operation, assists the muscle to contract in response to the detected information and the detected muscle contraction timing.

4 Claims, 12 Drawing Sheets

(56) References Cited

FOREIGN PATENT DOCUMENTS

| | | |
|---|---|---|
| JP | 2001-054507 | 2/2001 |
| JP | 2002-238930 | 8/2002 |
| JP | 2007-300112 | 11/2007 |
| JP | 2009-048837 | 3/2009 |
| JP | 2010-264174 | 11/2010 |
| JP | 2011-010698 | 1/2011 |
| JP | 2011-505897 | 3/2011 |
| JP | 2013-168575 | 8/2013 |
| WO | 2012/137897 | 10/2012 |
| WO | 2013/096260 A1 | 6/2013 |

OTHER PUBLICATIONS

Shinya Kuno, "Relationship between muscle cross-sectional area offemoral muscle and ability to run at full speed and ability to walk", Journal of the Society of Biomechanisms Japan, vol. 24, No. 3, pp. 148-152, Aug. 1, 2000.

Shoh Mitomo et al, "Effect of a combination of aerobic exercise and low-frequency electrical stimulation performed on a healthy person on exercise tolerance and muscle strength", the Journal of Japan Academy of Health Science, vol. 16, No. 2, pp. 66-72, 2013.

Takanori Kiyokura et al., "Wearable Laser Blood Flowmeter" NTT Technical Review, pp. 25-27, Nov. 2005.

The Partial European Search Report dated Jun. 19, 2015 for the related European Patent Application No. 15152420.4.

| 511 | 512 | 513 |
|---|---|---|
| MUSCLE | MUSCLE POTENTIAL SENSOR | EMS ELECTRODE PAIR |
| RIGHT ADDUCTOR MUSCLE | FIRST AND SECOND MUSCLE POTENTIAL SENSORS | FIRST AND SECOND EMS ELECTRODE PAIRS |
| LEFT ADDUCTOR MUSCLE | THIRD AND FOURTH MUSCLE POTENTIAL SENSORS | THIRD AND FOURTH EMS ELECTRODE PAIRS |
| RIGHT SARTORIUS MUSCLE | FIFTH POTENTIAL SENSOR | FIFTH ELECTRODE PAIR |
| LEFT SARTORIUS MUSCLE | SIXTH POTENTIAL SENSOR | SIXTH ELECTRODE PAIR |
| ••• | ••• | ••• |
| ⋮ | ••• M-TH POTENTIAL SENSOR | ••• N-TH ELECTRODE PAIR |

| MUSCLE | LOW-FREQUENCY COMPONENT RATIO THRESHOLD VALUE | | | |
|---|---|---|---|---|
| | FIRST USER TYPE | SECOND USER TYPE | ... | K-TH USER TYPE |
| ADDUCTOR MUSCLE | $\alpha_{11}$ | $\alpha_{21}$ | ⋮ | $\alpha_{K1}$ |
| SARTORIUS MUSCLE | $\alpha_{12}$ | $\alpha_{22}$ | ⋮ | $\alpha_{K2}$ |
| QUADRICEPS MUSCLE | $\alpha_{13}$ | $\alpha_{23}$ | ⋮ | $\alpha_{K3}$ |
| TRICEPS SURAE MUSCLE | $\alpha_{14}$ | $\alpha_{24}$ | ⋮ | $\alpha_{K4}$ |
| TIBIALIS ANTERIOR MUSCLE | $\alpha_{15}$ | $\alpha_{25}$ | ⋮ | $\alpha_{K5}$ |
| GLUTEUS MAXIMUS MUSCLE | $\alpha_{16}$ | $\alpha_{26}$ | ⋮ | $\alpha_{K6}$ |
| BICEPS FEMORIS MUSCLE | $\alpha_{17}$ | $\alpha_{27}$ | ⋮ | $\alpha_{K7}$ |
| ... | ... | ... | ... | ... |

FIG. 11

| MUSCLE | EMS ELECTRODE PAIR | ASSIST MOVEMENT |
|---|---|---|
| RIGHT ADDUCTOR MUSCLE | FIRST AND SECOND EMS ELECTRODE PAIRS | NO |
| LEFT ADDUCTOR MUSCLE | THIRD AND FOURTH EMS ELECTRODE PAIRS | NO |
| RIGHT SARTORIUS MUSCLE | FIFTH ELECTRODE PAIR | YES |
| LEFT SARTORIUS MUSCLE | SIXTH ELECTRODE PAIR | YES |
| ... | ... | ... |

611　612　613

610

MUSCLE SUPPORTER AND MUSCLE SUPPORT METHOD

CROSS REFERENCES TO RELATED APPLICATIONS

This application claims priority to Japanese Patent Application No. 2014-022413, filed on Feb. 7, 2014, the contents of which are hereby incorporated by reference.

BACKGROUND

1. Technical Field

The present invention relates to a muscle supporter and a muscle support method.

2. Description of the Related Art

Japanese Unexamined Patent Application Publication No. 2002-238930 discloses a texture member having elasticity and worn on the human body to assist a muscle to contract. Such a texture member (hereinafter referred to as a "muscle supporter") finds applications in a variety of fields.

The muscle supporter disclosed in Japanese Unexamined Patent Application Publication No. 2002-238930 is the texture member having a three-dimensional structure covering the waist. In the related art, if a user stoops forward at the waist, the elasticity of the texture member applies force to straighten the user's back. With the related art technique, the user is enabled to straighten his or her back with smaller muscle strength. In other words, the texture member assists the user to perform normal activities of daily life and exercise.

Related art techniques are not possibly support muscle in an effective way.

SUMMARY

One non-limiting and exemplary embodiment provides a muscle supporter that effectively supports muscle.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature a muscle supporter. The muscle supporter includes a sheet member attachable to skin covering a muscle. The muscle supporter includes the muscle strength condition detector that is disposed on the sheet member and detects information related to muscle strength condition of the muscle. The muscle supporter includes a muscle contraction timing detector that is disposed on the sheet member and that, in operation, detects a muscle contraction timing of the muscle. The muscle supporter includes a muscle assist movement provider that is disposed on the sheet member and that, in operation, assists the muscle to contract in response to the detected information and the detected muscle contraction timing.

The muscle supporter of the disclosure effectively supports a muscle.

These general and specific aspects may be implemented using a system, a method, and a computer program, and any combination of systems, methods, and computer programs.

BRIEF DESCRIPTION OF THE DRAWINGS

FIG. 7 illustrates an example of a block information table of the second embodiment;

FIG. 8 illustrates an example of a muscle strength condition determination table of the second embodiment;

FIG. 11 illustrates an example of detection result information in the second embodiment.

DETAILED DESCRIPTION

Underlying Knowledge Forming Basis of the Present Disclosure

There are times when elasticity of the texture member of related art is not high enough to perform a desired movement if a muscle is too weak in strength. The elasticity of the texture member is not excessively increased because a highly elastic texture member may interfere with the movement of another muscle or may increase compression too much on the body of a user. If variations in the muscle strength among multiple muscles related to one movement are too large, it is difficult to perform appropriate muscle support in the related art. In other words, the related art technique has difficulty in performing effective muscle support.

Embodiments of the disclosure are described in detail with reference to the drawings.

First Embodiment

A first embodiment of the disclosure is one of the basic aspects of the disclosure.

Figure 1:
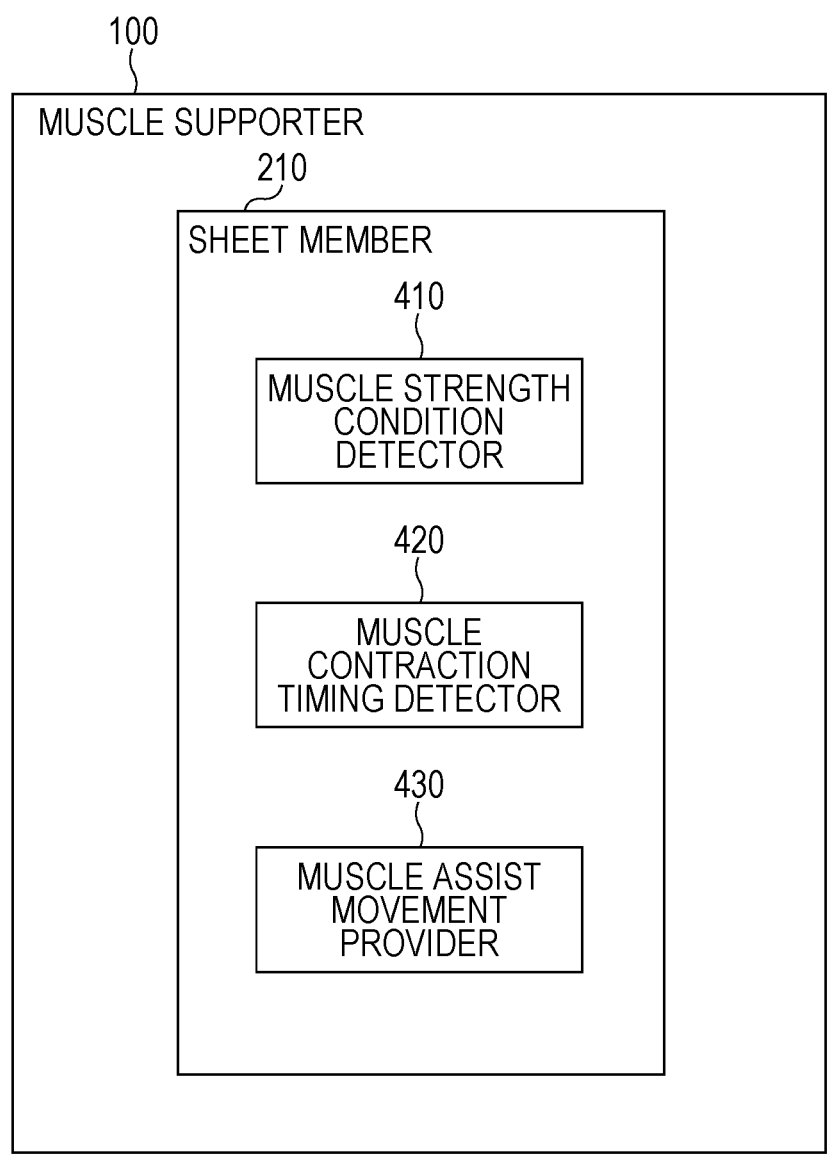
FIG. 1 is a block diagram illustrating a configuration of a muscle supporter of a first embodiment of the disclosure.

FIG. 1 illustrates an example of a configuration of a muscle supporter 100 of the first embodiment.

As illustrated in FIG. 1, the muscle supporter 100 includes a sheet member 210. The muscle supporter 100 further includes a muscle strength condition detector 410, a muscle contraction timing detector 420, and a muscle assist movement provider 430, all included in the sheet member 210.

The sheet member 210 is to be closely attached to skin covering a muscle.

The muscle strength condition detector 410 detects a muscle strength condition of the muscle.

The muscle contraction timing detector 420 detects a muscle contraction timing of the muscle.

The muscle assist movement provider 430 performs an assist movement to assist the muscle to contract in accordance with the detected muscle strength condition and the detected muscle contraction timing.

The muscle supporter 100 includes a central processing unit (CPU), a storage medium, such as a read-only memory (ROM) that stores a control program, and a working memory, such as a random-access memory (RAM), though these elements are not illustrated. The muscle supporter 100 includes a sensor that detects the muscle strength condition and the muscle contraction timing, and a movement element that performs the assist movement on the muscle. In this configuration, functions of these elements are implemented when the CPU executes the control program to control the operation of each of the sensor and the movement element.

Since the muscle supporter 100 assists the muscle to contract in accordance with the muscle strength condition and the muscle contraction timing, muscle support is effectively performed.

Second Embodiment

A second embodiment is a specific example of aspect where the disclosure is applied to a muscle supporter covering the two legs.

External View and Configuration of Muscle Supporter

External view and configuration of a muscle supporter of the second embodiment are described blow.

External View of Muscle Supporter

Figure 2:
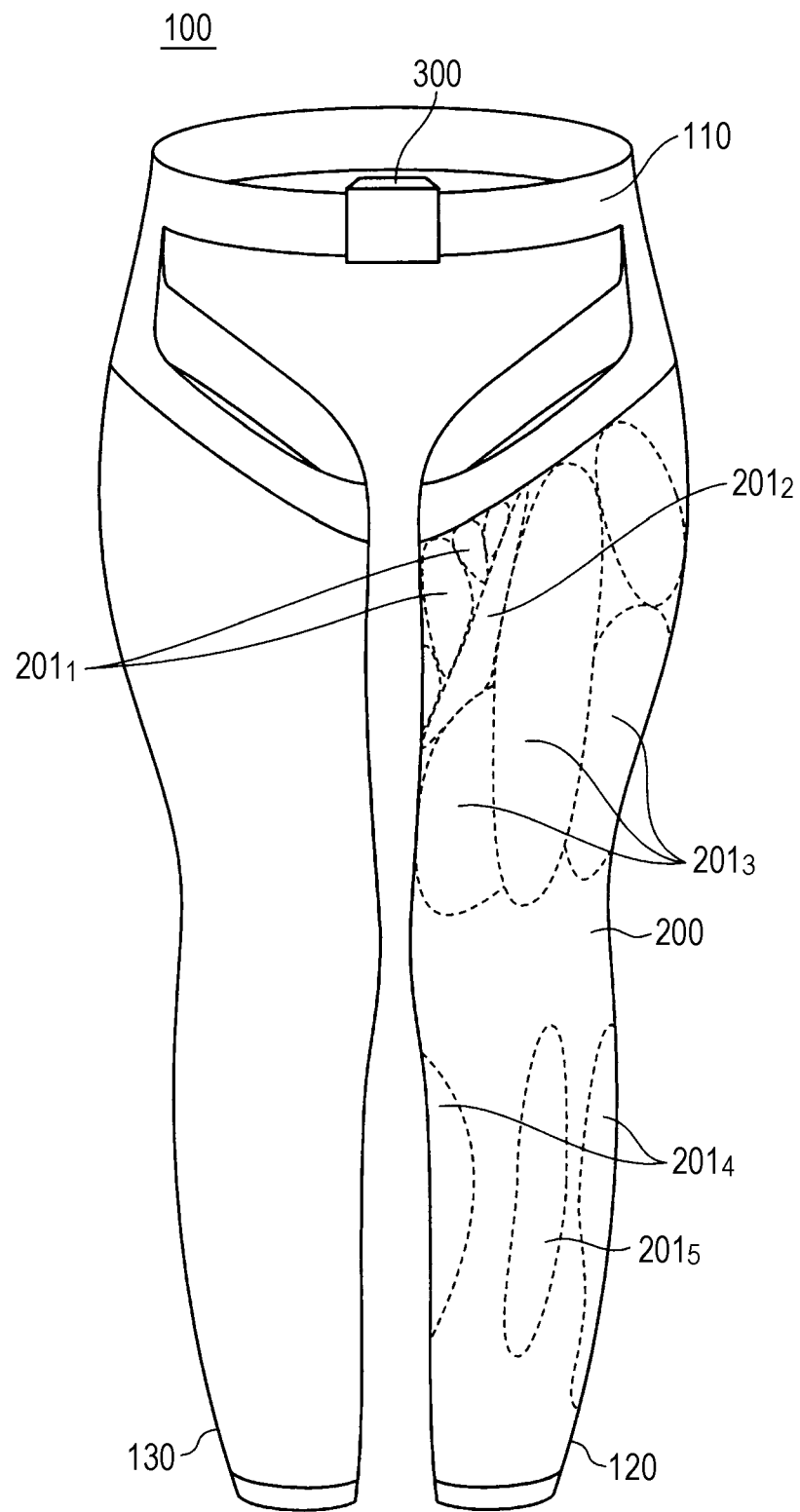
FIG. 2 is a front view illustrating a muscle supporter of a second embodiment of the disclosure.
Figure 3:
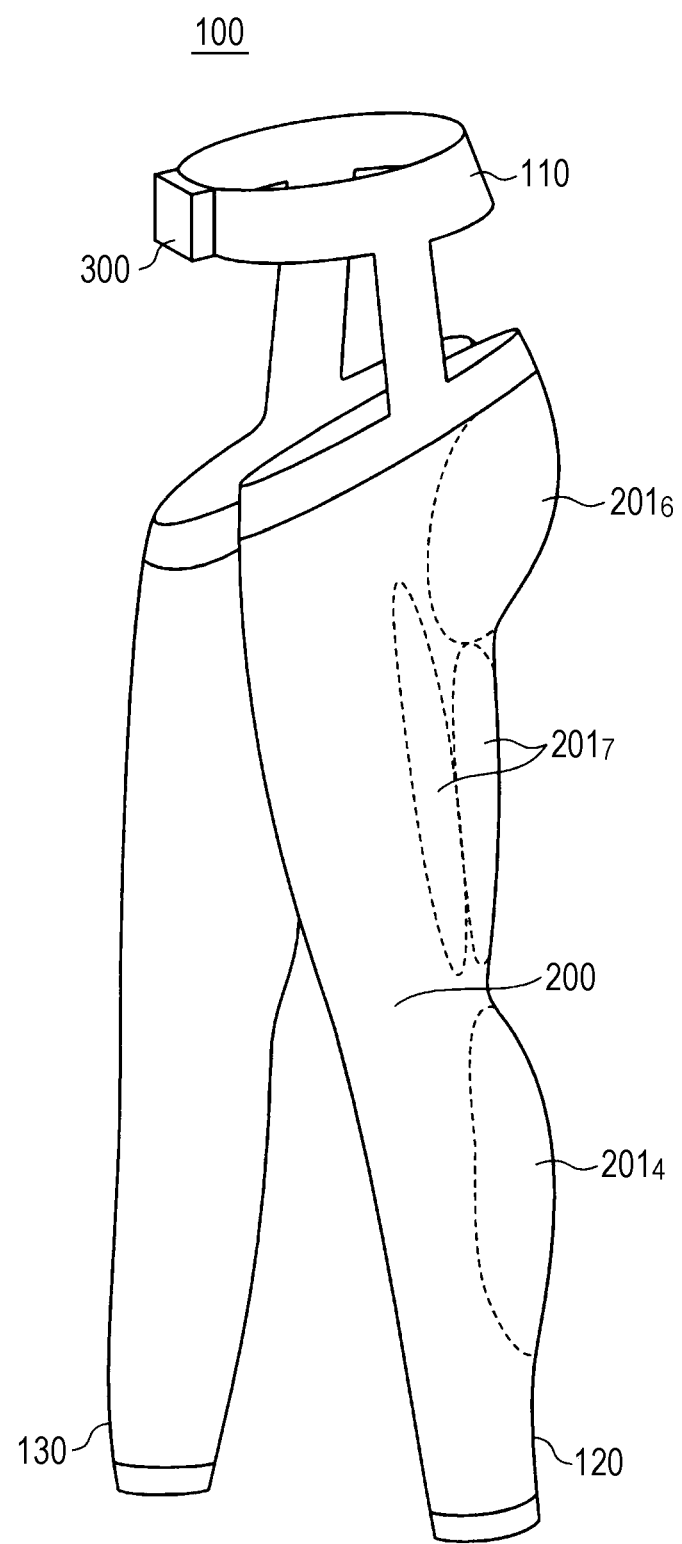
FIG. 3 is a side view illustrating the muscle supporter of the second embodiment of the disclosure.

FIG. 2 and FIG. 3 are external views of the muscle supporter of the second embodiment. FIG. 2 is a front view of the muscle supporter. FIG. 3 is a side view of the muscle supporter.

As illustrated in FIG. 2 and FIG. 3, the muscle supporter 100 is a tights-like supporter that includes a hip portion 110, a right leg portion 120 and a left leg portion 130. The hip portion 110 is a belt-like portion that is secured to the hip of the user. The right leg portion 120 is cylindrical and is secured to generally cover a portion of the right leg upward from the lower portion of the right shank. The left leg portion 130 is cylindrical and is secured to generally cover a portion of the left leg upward from the lower portion of the left shank. The right leg portion 120 and the left leg portion 130 are connected to the hip portion 110.

The right leg portion 120 and the left leg portion 130 are manufactured of a texture member that is flexible, expandable, and elastic. At least a portion of the texture member includes a sheet device that includes multiple compact sensors and multiple movement elements. The compact sensors and movement elements are arranged to effectively assist the muscle to contract. In the second embodiment, the right leg portion 120 and the left leg portion 130 are referred to as a "sheet device 200" as a whole unit including a portion where neither sensor nor movement element is arranged. The sheet device 200 including the sensor and the movement element is described in detail below.

The texture member may be configured so that the muscles of the right leg and the left leg are assisted to contract. In other words, the muscle supporter 100 may additionally have a function of a commercially available muscle supporter.

The muscle supporter 100 includes a controller 300 that is to be arranged on the abdominal side of the hip portion 110. The controller 300 is a device protected by a housing manufactured of a material, such as a plastic. As described below, the controller 300 is connected to each of the sensors and the movement elements via signal lines (not illustrated). The controller 300 has a function of controlling the sensors and movement elements.

Configuration of Sheet Device

Figure 4:
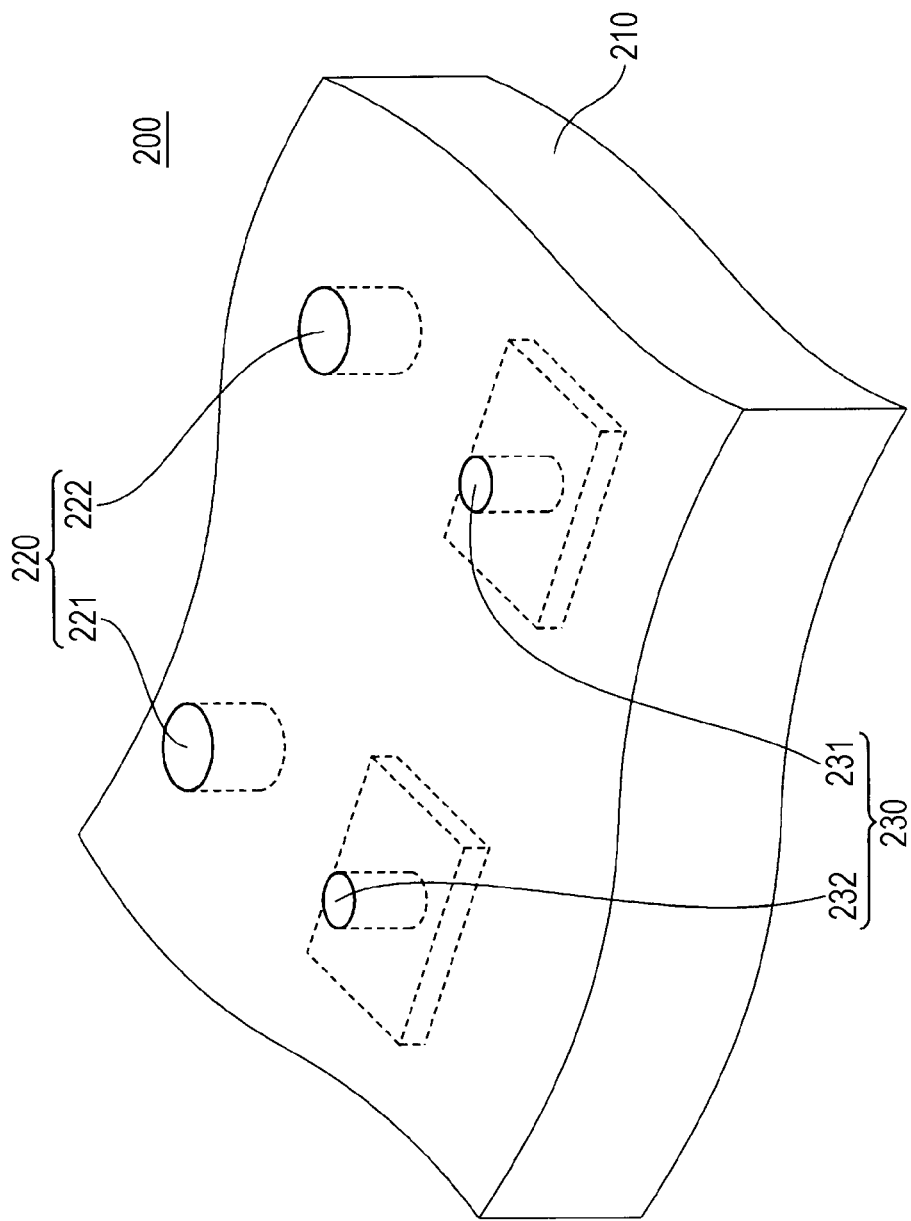
FIG. 4 illustrates an example of a structure of a sheet device of the second embodiment.

FIG. 4 illustrates an example of a configuration of the sheet device 200. FIG. 4 illustrates a portion of the sheet device 200.

Referring to FIG. 4, the sheet device 200 includes a sheet member 210, and a muscle potential sensor 220 and an electrical muscle stimulation (EMS) electrode pair 230 embedded in the sheet member 210.

The sheet member 210 is expandable and flexible and has a thickness of several millimeters. The sheet member 210 is designed to remain attached to the skin with surface tension. The sheet member 210 may be manufactured of a set material of an energy radiation beam setting composition containing acryloyl group, terminated polyurethane polymer and acrylic monomer (see Japanese Unexamined Patent Application Publication No. 2013-168575). To ensure sufficient adhesion, a biocompatible adhesive, such as spirit gum, silicone adhesive, or latex adhesive, may be used.

The muscle potential sensor 220 includes a first muscle potential detection electrode 221 and a second muscle potential detection electrode 222. The muscle potential sensor 220 detects a voltage between the first muscle potential detection electrode 221 and the second muscle potential detection electrode 222 as a muscle potential of the muscle beneath the skin which the first and second muscle potential detection electrodes 221 and 222 are in contact with.

The electrode surface of each of the first muscle potential detection electrode 221 and the second muscle potential detection electrode 222 are exposed on the inner side of the sheet member 210 attached to the skin (hereinafter referred to as an "inner surface"). In other words, with the muscle supporter 100 worn on the body of the user, the muscle potential sensor 220 is in contact with the skin and detects the muscle potential of the muscle near the muscle potential sensor 220. The muscle potential sensor described in Japanese Unexamined Patent Application Publication No. 2010-264174 may be used for the muscle potential sensor 220, for example.

The EMS electrode pair 230 includes a positive EMS electrode 231 and a negative EMS electrode 232. The EMS electrode pair 230 causes a weak current to flow through the muscle between the positive EMS electrode 231 and the negative EMS electrode 232 in order to assist the muscle to contract.

The electrode surface of each of the positive EMS electrode 231 and the negative EMS electrode 232 is internally exposed on the inner side of the sheet member 210. More specifically, with the muscle supporter 100 worn on the body of the user, the EMS electrode pair 230 is in contact with the skin and, via the skin, assists the muscle near the EMS electrode pair 230 to contract. The EMS electrode pair described in Japanese Unexamined Patent Application Publication No. 4-312472 may be used for the EMS electrode pair 230.

The sheet device 200 is arranged on a predetermined region (hereinafter referred to as a block) corresponding to each muscle. More specifically, the sheet device 200 detects a muscle potential and assists contraction on a per muscle basis.

Each block is an area enclosed by a broken line as illustrated in FIG. 2 and FIG. 3. Blocks $201_1$ through $201_7$ respectively correspond to the locations of the adductor muscle, the sartorius muscle, the quadriceps muscle, the triceps surae muscle, the tibialis anterior muscle, the gluteus maximus muscle, and the biceps femoris muscle. FIG. 2 and FIG. 3 illustrate the left leg portion 130. The blocks are equally set up in the right leg portion 120 and the left leg portion 130 (in a bilaterally symmetrical way).

Figure 5:
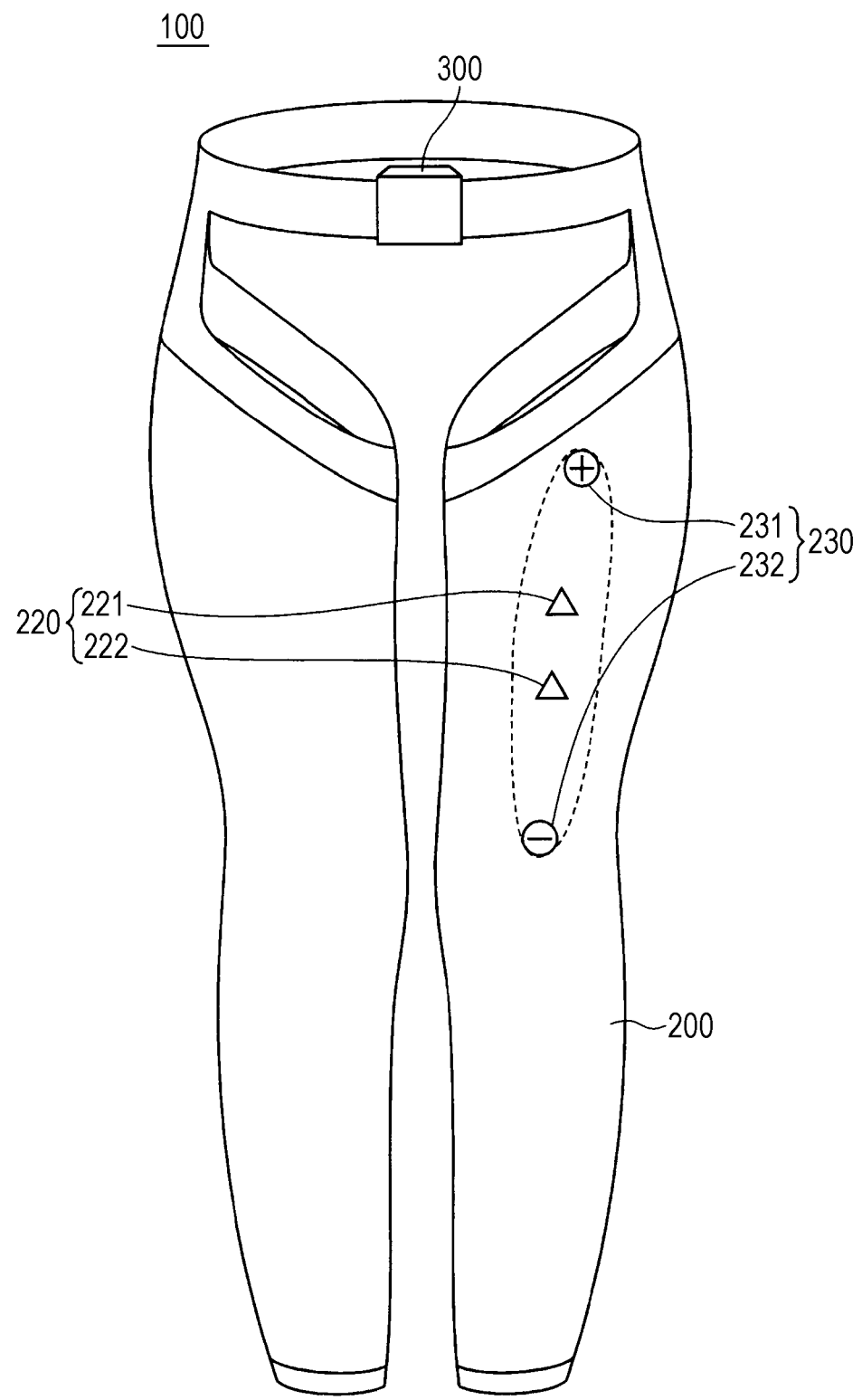
FIG. 5 illustrates an example of a layout of a muscle potential sensor and an electronic muscle simulation (EMS) electrode pair in the second embodiment.

FIG. 5 illustrates an example of the layout of the muscle potential sensor 220 and the EMS electrode pair 230 in a block. FIG. 5 illustrates the block $201_3$ corresponding to the adductor muscle of the left leg.

Referring to FIG. 5, the first and second muscle potential detection electrodes 221 and 222 of the muscle potential sensor 220 (see FIG. 4), spaced from each other by several centimeters, are arranged near the center of the muscle (the center of the block). The positive EMS electrode 231 of the EMS electrode pair 230 is arranged near one end of the muscle (one end of the block) in the direction of expansion and contraction of the muscle. The negative EMS electrode 232 of the EMS electrode pair 230 is arranged near the other end of the muscle (the other end of the block) in the direction of expansion and contraction of the muscle. Relationship between muscle potential, and muscle contraction and muscle strength condition The relationship between the muscle potential detected by the muscle potential sensor 220 and the muscle contraction and the muscle strength condition is described below.

Cells of the muscle are separated by cell membranes, and are largely divided an intracellular region and an extracellular region. The cell membrane is close to an insulator in property, and the intracellular region and the extracellular region are respectively filled with an intracellular fluid and an extracellular fluid, each of which is an electrolyte solution. The intracellular region in the insulator (cell membrane) and the extracellular region outside the insulator are different in ion concentration. If the degree of contraction of the muscle changes, ion exchange is performed between the intracellular region and the extracellular region of the muscle. A weak potential thus results. Weak potentials occurring in the cells are aggregated over the entire muscle, becoming a potential of several mV on the skin surface. The muscle potential sensor 220 detects as the muscle potential such a potential occurring on the skin surface.

The level of the muscle potential detected by the muscle potential sensor 220 responds to a change in the degree of contraction of the muscle, in other words, the contraction or expansion of the muscle. The polarity of the potential is reversed between when the muscle contracts and when the muscle expands.

The muscles include slow muscle and fast muscles. Time data of the muscle potential caused by these muscles (hereinafter referred to as a "muscle potential signal") is very random. The muscle potential signal is characterized by the feature that a high-frequency component is predominant in the muscle potential signal of the fast muscle, and that a low-frequency component is predominant in the muscle potential signal of the slow muscle. The muscle is also characterized by the feature that with age, the muscle weakens and the ratio of the fast muscles decreases while the ratio of the slow muscles increases (see the Society of Physical Therapy Science Japan "Exercise Therapy", sixth edition, p. 36, Mar. 1998).

The muscle potential signal detected by the muscle potential sensor 220 indicates that a high ratio of the low frequency component means a weakened muscle strength.

In the second embodiment, a low-frequency component ratio is used as an index value indicating the level of the muscle strength. The low-frequency component ratio is a ratio of an integral value of a low-frequency component to an integral value of an entire bandwidth component.

The muscle contraction timing and the muscle strength of each muscle are determined from the muscle potential detected by the muscle potential sensor 220. The muscle contraction timing refers to a timing the muscle contracts in response to a signal from the brain, in other words, the moment the user tightens the muscles or the duration during which the user keeps tightening the muscles.

The muscle supporter 100 detects the muscle strength condition and the muscle contraction timing of each muscle from the detection results from the muscle potential sensor 220. The muscle supporter 100 operates the corresponding EMS electrode pair 230 at the same timing the user uses a muscle having a weak strength, thereby assisting the muscle to contract. This process is performed by the function of the controller 300 (see FIG. 2, FIG. 3 and FIG. 5).

In the second embodiment, the sheet device 200 includes M muscle potential sensors 220 and N EMS electrode pairs 230.

Functional Configuration of Muscle Supporter

Figure 6:
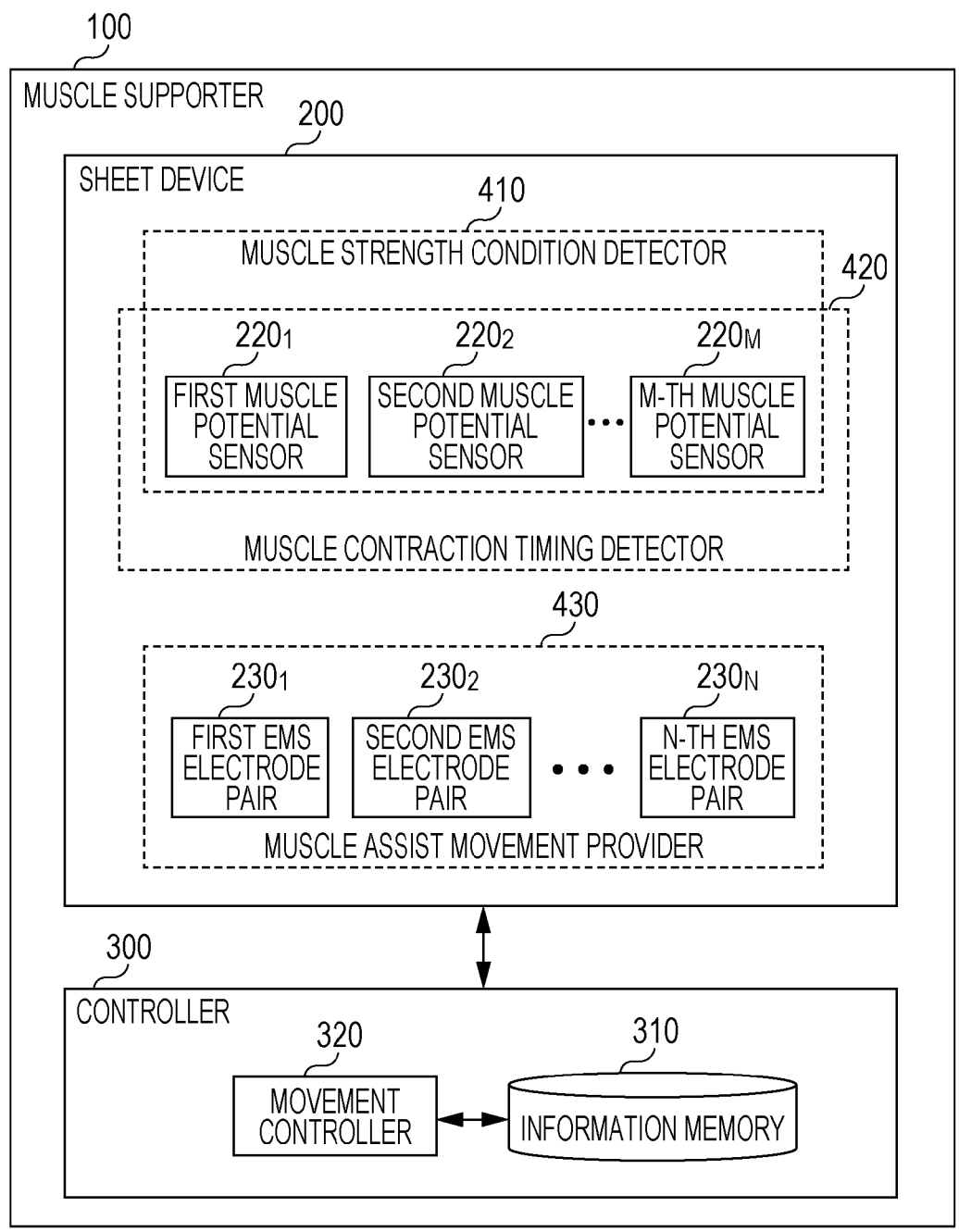
FIG. 6 illustrates a functional configuration of the muscle supporter of the second embodiment.

FIG. 6 illustrates an example of a functional configuration of the muscle supporter 100.

The muscle supporter 100 includes first through M-th muscle sensors $220_1$ through $220_M$, and first through N-th EMS electrode pairs $230_1$ through $230_N$ arranged in the sheet device 200, and an information memory 310 and a movement controller 320 arranged in the controller 300.

The muscle supporter 100 includes, in the sheet device 200, a muscle strength condition detector 410, a muscle contraction timing detector 420, and a muscle assist movement provider 430.

The muscle strength condition detector 410 includes the first through M-th muscle sensors $220_1$ through $220_M$. The muscle strength condition detector 410 detects the muscle potential signal of the muscle potential sensor 220 as information indicating the muscle strength condition of the corresponding muscle.

The muscle contraction timing detector 420 includes the first through M-th muscle sensors $220_1$ through $220_M$. The muscle contraction timing detector 420 detects a muscle potential signal of the muscle potential sensor 220 as information indicating the muscle contraction timing of the corresponding muscle.

The muscle assist movement provider 430 includes the first through N-th EMS electrode pairs $230_1$ through $230_N$. Under the control of the movement controller 320 to be discussed below, the muscle assist movement provider 430 performs the assist movement to assist the muscle to contract, based on the detected muscle strength condition and muscle contraction timing.

The information memory 310 pre-stores a block information table and a muscle strength condition determination table. The block information table associates the muscle potential sensor 220 and EMS electrode pair 230 with the block 201 (see FIG. 2 and FIG. 3). The muscle strength condition determination table indicates determination criteria according to which a determination is performed as to whether each muscle weakens to a muscle support level.

FIG. 7 illustrates a block information table 510.

Referring to FIG. 7, the block information table 510 associates identification information 511 of the muscle corresponding to a block 201 with identification information 512 of the muscle potential sensor 220 and identification information 513 of the EMS electrode pair 230 placed in the block 201.

The muscle whose muscle potential is detected by the first and second muscle potential sensors $220_1$ and $220_2$ is identical to the muscle that the first and second EMS electrode pairs $230_1$ and $230_2$ assist to contract.

The operation of the EMS electrode pair 230 is controlled in accordance with the detection results of the muscle potential sensor 220 by referencing the block information table 510. The assist movement is thus performed on a per muscle basis in accordance with the muscle strength condition and the muscle contraction timing.

FIG. 8 illustrates a muscle strength condition determination table 520.

Referring to FIG. 8, the muscle strength condition determination table 520 associates identification information 521 of each muscle with a low-frequency component ratio threshold value 523 on each user type 522.

The user type 522 is defined by age, sex, or the like, and is expressed by "women in their 40s" or "men in their 60s", for example. The low-frequency component ratio threshold value 523 is a threshold value of the low-frequency component ratio, and is a determination criterion according to which a determination is performed as to whether the muscle weakens to a level in need of muscle support. The low-frequency component ratio threshold value 523 is a mean value of the low-frequency component ratios acquired from a large number of subjects having an average muscle strength in the user type 522.

A low-frequency component ratio $\alpha_{11}$ is listed for a combination of the identification information 521 of the "adductor muscle" and a "first user type" as the user type 522. This is interpreted to mean that the user belongs to the first user type, that if the low-frequency component ratio detected from the adductor muscle of the user is $\alpha_{11}$ or above, the muscle strength is weak and the muscle support is to be performed.

An appropriate assist movement responsive to the muscle strength is performed by referencing the muscle strength condition determination table 520 and by determining whether to perform the muscle support.

The movement controller 320 of FIG. 6 is respectively connected to the first through M-th muscle sensors $220_1$ through $220_M$ and the first through N-th EMS electrode pairs $230_1$ through $230_N$ via signal lines (not illustrated) embedded in the hip portion 110 and the sheet device 200 in the muscle supporter 100 (see FIG. 2 and FIG. 3).

The movement controller 320 outputs a control signal to the muscle potential sensor 220 to control the operation of the muscle potential sensor 220, and receives a detection value output from the muscle potential sensor 220. The movement controller 320 also outputs a control signal to each EMS electrode pair 230 to control the operation of the EMS electrode pair 230.

The movement controller 320 determines a muscle serving as a target of the support movement by EMS (hereinafter referred to as a "support target muscle") based on the muscle potential signal of each muscle potential sensor 220, and the block information table 510 and the muscle strength condition determination table 520 stored on the information memory 310. The movement controller 320 detects the muscle contraction timing of the support target muscle based on the muscle potential signal of each muscle potential sensor 220, and performs the muscle assist movement by causing the corresponding EMS electrode pair 230 to operate.

In the second embodiment, the movement controller 320 operates in one of the two modes, namely, the detection mode and the support mode. The detection mode is an operation mode that determines a support target muscle. The support mode is an operation mode that performs the muscle support on the support target muscle determined in the detection mode.

The controller 300 includes a CPU, a storage media, such as a ROM storing a control program, and a working memory, such as a RAM. These elements are not illustrated. Functions of the controller 300 are implemented when the CPU executes the control program.

The controller 300 further includes a power supply, and an operation unit, such as a keyswitch, though these elements are not illustrated. The power supply supplies power to cause the CPU and the sheet device 200 to operate. The operation unit receives from the user a variety of operations including an operation instruction to start the detection mode, and an operation instruction to start the support mode.

In this configuration, the muscle supporter 100 performs the muscle support by EMS on each of the multiple muscles in response to the muscle strength condition and the muscle contraction timing.

Process of Muscle Supporter

The process of the muscle supporter 100 is described below. The operation of the muscle supporter 100 is mainly controlled by the movement controller 320.

Figure 9:
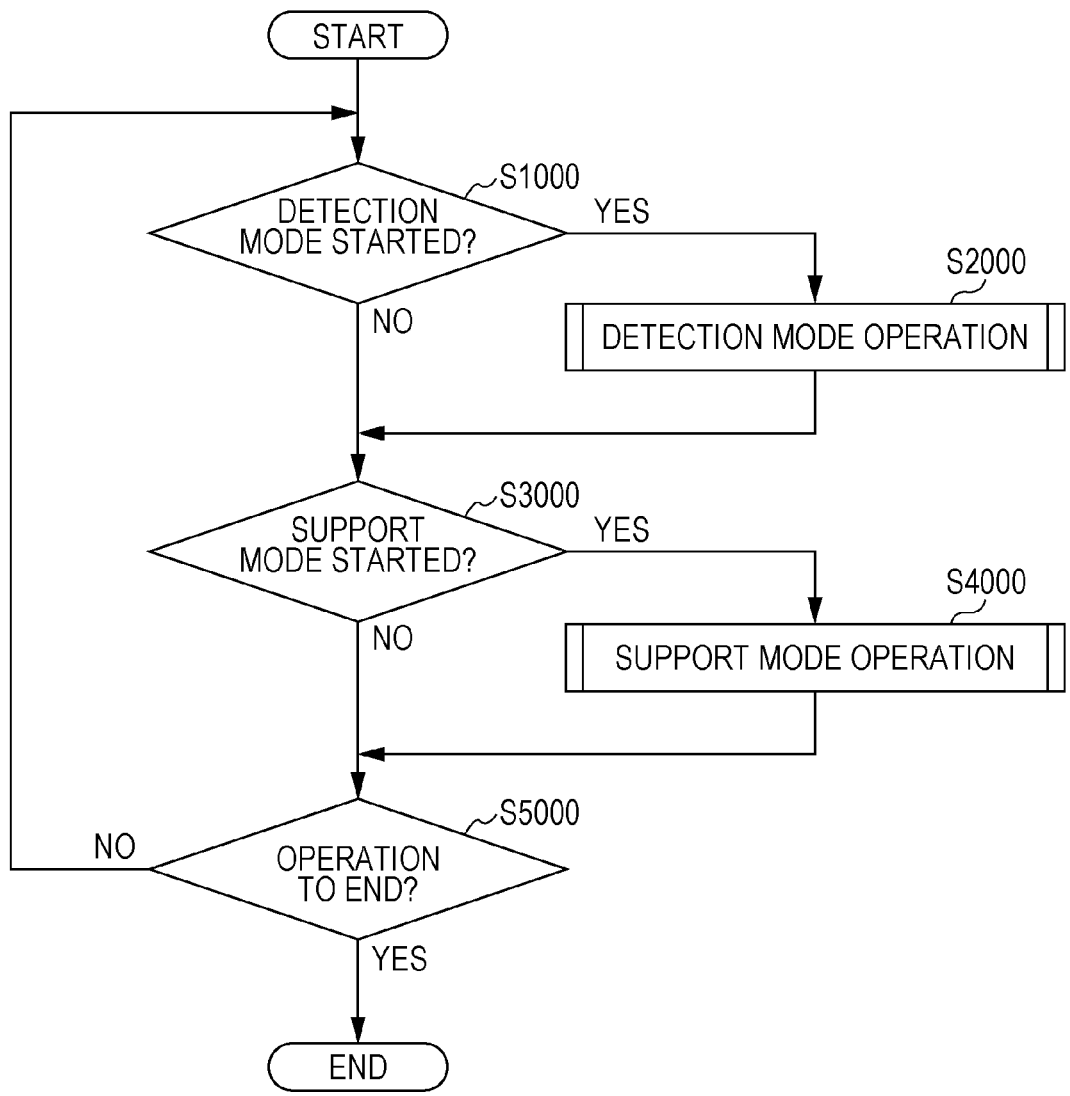
FIG. 9 is a flowchart illustrating an operation example of the muscle supporter of the second embodiment.

FIG. 9 is a flowchart illustrating an example of the operation of the muscle supporter 100. In response to a power-on with the muscle supporter 100 worn on the body of the user, the muscle supporter 100 starts the operation described below.

In step S1000, the movement controller 320 determines whether an operation to instruct the start of the muscle supporter 100 in the detection mode has been performed. If the operation has been performed (yes branch from S1000), processing proceeds to step S2000. If no such operation has been performed (no branch from S1000), processing proceeds to step S3000.

In step S2000, the movement controller 320 operates in the detection mode (hereinafter referred to as a "detection mode operation"), and then proceeds to step S3000. The detection mode operation is described in detail below.

In step S3000, the movement controller 320 determines whether an operation to instruct the start of the muscle supporter 100 in the support mode has been performed. If such an operation has been performed (yes from step S3000), processing proceeds to step S4000. If no such operation is performed (no branch from step S3000), the movement controller 320 proceeds to step S5000.

In step S4000, the movement controller 320 performs an operation in the support mode (hereinafter referred to as a "support mode operation"), and then proceeds to step S5000. The support mode operation is described in detail below.

In step S5000, the movement controller 320 determines whether the user has instructed the muscle supporter 100 to end the operation. If the instruction to end the operation has not given by the user (no branch from S5000), the movement controller 320 returns to step S1000. If the instruction to end the operation is given by the user (yes branch from S5000), the movement controller 320 ends a series of operations.

Through this process, in response to the instruction from the user, the muscle supporter 100 operates switchably between the detection mode to determine the support target muscle and the support mode to perform the muscle support to the support target muscle.

Figure 10:
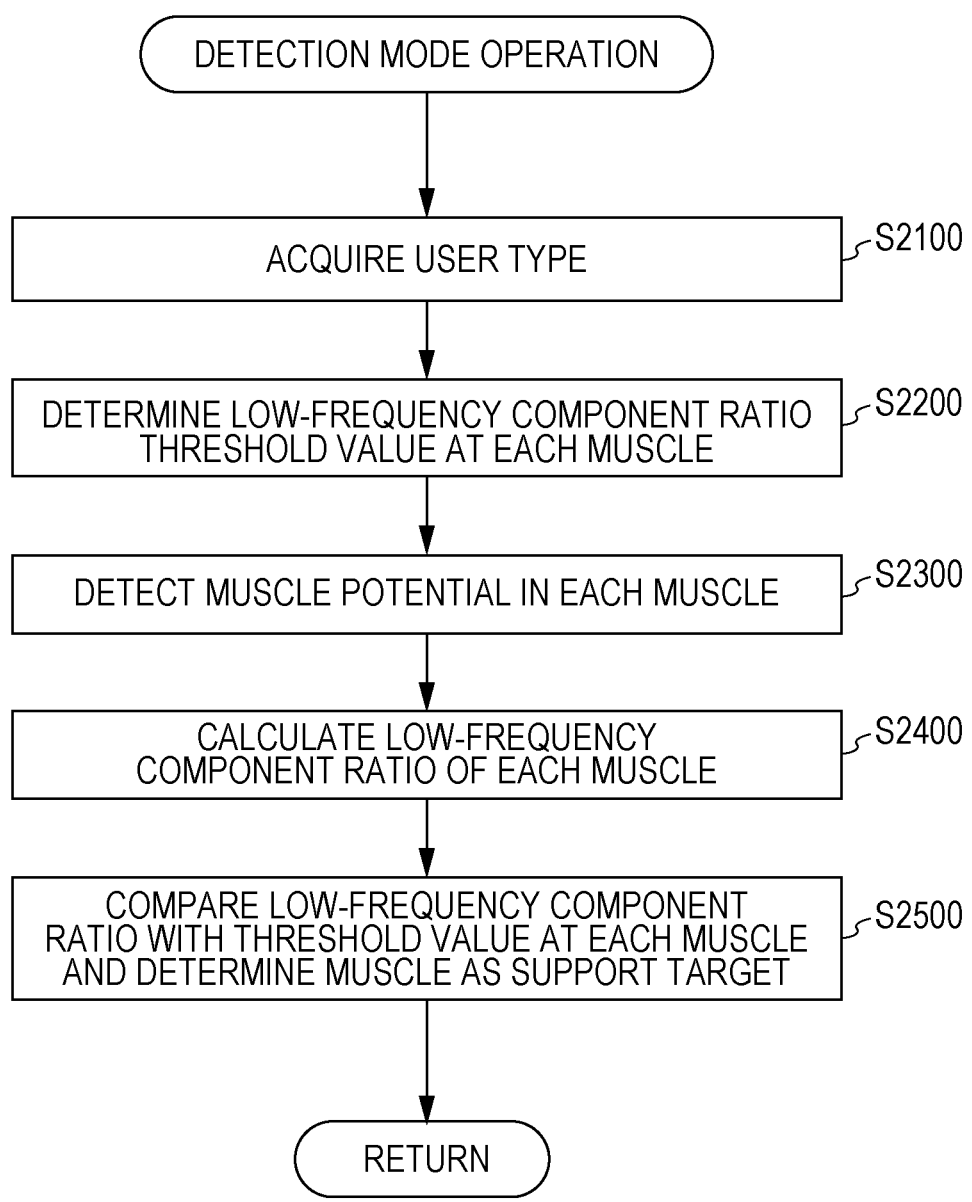
FIG. 10 is a flowchart illustrating an operational example of a detection mode in the second embodiment.

FIG. 10 is a flowchart illustrating an example of the detection mode operation (in step S2000 of FIG. 9).

In step S2100, the movement controller 320 acquires the user type the user belongs to. The user type corresponds to the user type 522 in the muscle strength condition determination table 520 (see FIG. 8). The movement controller 320 acquires the user type by receiving an input related to age and sex, for example.

In step S2200, the movement controller 320 references the muscle strength condition determination table 520 and, in accordance with the acquired user type, determines the low-frequency component ratio that is applicable to the user on a per muscle basis.

In step S2300, the movement controller 320 causes the first through M-th muscle sensors $220_1$ through $220_M$ to detect the muscle potentials of the muscles of the user, and acquires the muscle potential signals of the muscles.

In step S2400, the movement controller 320 calculates the low-frequency component ratio from the muscle potential signal of each muscle.

More specifically, the movement controller 320 applies a signal resulting from full-wave rectifying the muscle potential signal to a low-pass filter (having a cutoff frequency of 50 Hz, for example), thereby obtaining a low-frequency component signal. The movement controller 320 then divides a value resulting from integrating the low-frequency component signal by a value resulting from integrating the original muscle potential signal as the entire bandwidth component signal, thereby calculating the low-frequency component ratio.

The movement controller 320 may perform these calculation operations using analog circuits including a filter circuit, an integrating circuit, and a divider circuit. If the muscle potential signal is an analog signal, the calculation operations is performed through digital signal processing by CPU. In such a case, the movement controller 320 analog-to-digital (A/D) converts the muscle potential signal.

In step S2500, the movement controller 320 compares the calculated low-frequency component ratio with the determined low-frequency component ratio threshold value. The movement controller 320 determines a muscle having a low-frequency component ratio equal to or above the low-frequency component ratio threshold value as the support target muscle (namely, a muscle having a weak strength). The movement controller 320 ends the detection mode, and proceeds to step S3000 of FIG. 9.

In the detection mode operation, the muscle supporter 100 detects a muscle having a weak strength, and determines it as the support target muscle. The movement controller 320 stores determination results as detection result information on the information memory 310.

FIG. 11 illustrates detection result information 610.

As illustrated in FIG. 11, the detection result information 610 includes an assist movement status 613 as to whether to perform the assist movement in association with identification information 611 of the muscle or identification information 612 of the EMS electrode pair 230. By referencing the identification information 611, the movement controller 320 quickly determines whether each muscle is to be assisted or not or whether the EMS electrode pair 230 is to perform the assist movement.

Figure 12:
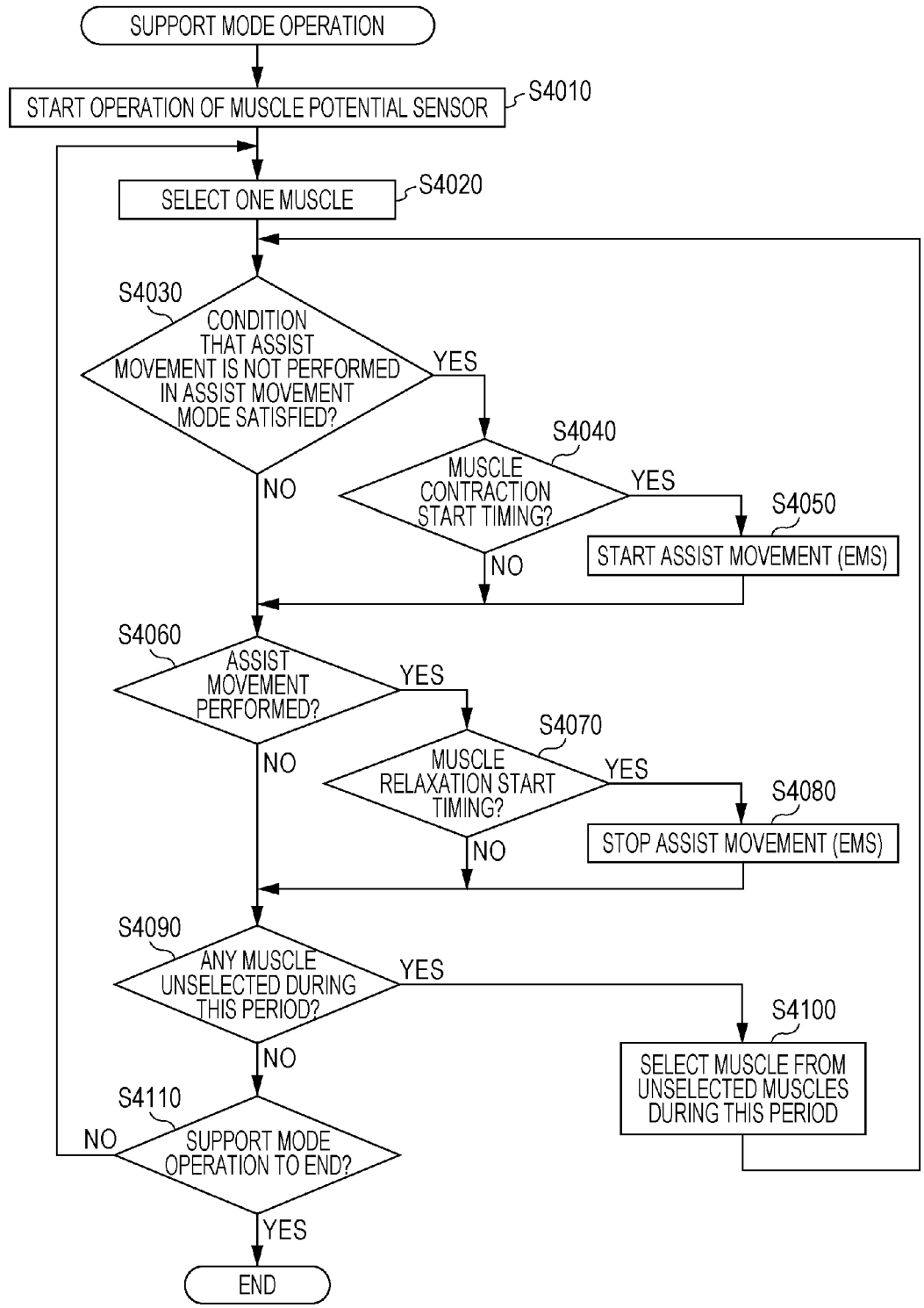
FIG. 12 is a flowchart illustrating an operational example of a support mode in the second embodiment.

FIG. 12 is a flowchart illustrating an example of the support mode operation (step S4000 of FIG. 9).

In step S4010, the movement controller 320 causes the first through M-th muscle sensors $220_1$ through $220_M$ to start the operations thereof. More specifically, the movement controller 320 starts acquiring the muscle potential signal of each muscle.

In step S4020, the movement controller 320 selects one from the multiple muscles corresponding to the block 201 (see FIG. 2 and FIG. 3) where the muscle potential sensor 220 and the EMS electrode pair 230 are arranged. The movement controller 320 treats as one process period a duration which the movement controller 320 takes to reach step S4110.

In step S4030, the movement controller 320 determines whether the selected muscle satisfies the condition that the muscle is to be assisted and that the assist movement is not in progress on the muscle. The determination as to whether the muscle is to be assisted is performed by referencing the detection result information 610 (see FIG. 11) stored on the information memory 310.

If the condition is satisfied (yes branch from step S4030), the movement controller 320 proceeds to step S4040. If the condition is not satisfied (no branch from step S4040), the movement controller 320 proceeds to step S4060.

In step S4040, the movement controller 320 determines, in response to the muscle potential signal, whether it is the timing to start the contraction of the muscle (hereinafter referred to as a "muscle contraction start timing").

More specifically, the movement controller 320 analyzes the muscle potential signal, and determines whether a muscle potential of a predetermined polarity corresponding to a muscle contraction direction is generated in the muscle potential sensor 220 corresponding to the selected muscle. The generation of the muscle potential refers to the state in which the muscle potential is above a predetermined value that is sufficient enough to determine that the muscle has started contracting.

If it is the muscle contraction start timing (yes branch from step S4040), the movement controller 320 proceeds to step S4050. If it is not the muscle contraction start timing (no branch fro step S4040), the movement controller 320 proceeds to step S4060.

In step S4050, the movement controller 320 starts the assist movement (EMS) on the selected muscle. More specifically, the movement controller 320 causes the corresponding EMS electrode pair 230 to start operating.

The EMS electrode pair 230 causes a weak current of about 1 mA to continuously flow through the muscle. Such a weak current mildly acts on the muscle in contraction.

The output values of the EMS electrode pairs 230 may be at the same level or at different levels (different on a per muscle basis). The output value of each EMS electrode pair 230 may be a fixed value or may be adjusted by a user operation. The movement controller 320 may vary the output value of the EMS electrode pair 230 in accordance with the level of the muscle strength determined from the detected muscle potential or in accordance with the user type.

In step S4060, the movement controller 320 determines whether the selected muscle is undergoing the assist movement (EMS) by the EMS electrode pair 230. If the selected muscle is undergoing the assist movement (EMS) by the EMS electrode pair 230 (yes branch from step S4060), the movement controller 320 proceeds to step S4070. If the selected muscle is not undergoing the assist movement (EMS) by the EMS electrode pair 230 (no branch from step S4060), the movement controller 320 proceeds to step 4090.

In step S4070, the movement controller 320 determines in response to the muscle potential signal whether it is a timing of starting a relaxation of the muscle (hereinafter referred to as a "muscle relaxation start timing").

More specifically, the movement controller 320 analyzes the muscle potential signal and determines whether a muscle potential having a polarity corresponding to a direction of muscle relaxation is generated in the muscle potential sensor 220. The generation of the muscle potential refers to the state in which the muscle potential is above a predetermined value that is sufficient enough to determine that the muscle has started relaxing.

The selected muscle is in the state that the EMS electrode pair 230 is currently performing EMS. If EMS is an alternating current, the mean level of the muscle potential is rippled by EMS. The movement controller 320 sets a threshold value that is sufficiently higher than a muscle potential caused by the ripple, and determines the muscle relaxation start timing on condition that the average level of the muscle potential is below the threshold value. The effect of EMS on the determination of the muscle relaxation start timing may be eliminated in this way.

If it is the muscle relaxation start timing (yes branch from S4070), the movement controller 320 proceeds to step S4080. If it is not the muscle relaxation start timing (no branch from S4070), the movement controller 320 proceeds to step S4090.

In step S4080, the movement controller 320 stops the assist movement (EMS) performed on the selected muscle. In other words, the movement controller 320 causes the corresponding EMS electrode pair 230 to stop.

In step S4090, the movement controller 320 determines in the current period whether an unselected muscle is present. If an unselected muscle is present (yes branch from step S4090), the movement controller 320 proceeds to step S4100. If no unselected muscle is present (no branch from step S4090), the movement controller 320 proceeds to step S4110.

In step S4100, the movement controller 320 selects one muscle from among the unselected muscles, and then proceeds to step S4030.

In step S4110, the movement controller 320 determines whether an instruction to stop the support movement has been given in response to a user operation. If the instruction to stop the support movement has not been given (no branch from step S4110), the movement controller 320 returns to step S4020. If the instruction to stop the support movement has been given (yes branch from step S4110), the movement controller 320 returns to step S5000 of FIG. 9.

Through such a support movement, the movement controller 320 detects, as the muscle contraction timing of performing the muscle support, at least a portion of a period extending from the muscle contraction start timing to the muscle relaxation start timing. At every muscle contraction timing, the muscle supporter 100 repeats the assist movement (EMS) on the support target muscle.

Effect of Muscle Supporter

The muscle supporter 100 thus assists the muscle to contact in accordance with the muscle strength condition and at the muscle contraction timing.

A human's fast muscle fibers may atrophy with age or for some other reasons, resulting in a weak muscle strength. Then, he or she may have difficulties in daily activities, including walking. For example, it is reported that persons in their 60s have a muscle cross-section area about 30 percent less than that of persons in their 20s (Shinya KUNO "Relationship between muscle cross-sectional area of femoral muscle and ability to run at full speed and ability to walk", Journal of the Society of Biomechanisms Japan, Vol. 24, No. 3, pp. 148-152, Aug. 1, 2000).

On the other hand, daily exercises may contribute to maintaining or improving the muscle strength. However, it is difficult for persons having the muscles of the entire body generally weakened, typically aged people, to perform daily exercises.

The related art muscle supporters perform the muscle support only by elasticity of the texture member. If a sufficient support force is used to assist a given exercise in such a muscle supporter, that support force may interfere with another exercise and excessive compression may be applied to the body. The excessive compression to the body may result in malfunctions of the body including a blood circulation failure, swelling, or disorder of sensation.

The use of EMS may contribute to maintaining or improving the muscle strength without the need for exercise. However, it is not so easy for a user to identify which muscle among the muscles used in daily activities is to be trained, based on the user's own sensation or the observation of another person. For this reason, there is a possibility that stimulation is applied to a muscle which is not to be trained. As a result, balance of the muscle strength could be destroyed.

In an actual operation, the muscle supporter 100 of the second embodiment assists a muscle having a weak strength to contract at the timing when the muscle is used. More specifically, the muscle supporter 100 performs the muscle support in view of variations in the muscle strength so that the daily activities are smoothly performed.

The muscle strength typically improves by repeating stimulation to the muscle through EMS or the like. The muscle supporter 100 of the second embodiment may improve the muscle strength of the user's body, and thus allows the user to perform the daily activities in a smoother fashion through the user's own muscle strength.

The muscle supporter 100 may assist the user to effectively perform the muscle support in a particular motion, such as a movement in a particular sport. In such a case, the muscle strength condition determination table 520 may be modified to support such a particular motion. The muscle supporter 100, if used in aerobic exercise, effectively strengthens the muscles (see Shoh MITOMO, Hitoshi TAKEI, Sayaka ISHII, and Kazuna ISHIKAWA "Effect of a combination of aerobic exercise and low-frequency electrical stimulation performed on a healthy person on exercise tolerance and muscle strength", the Journal of Japan Academy of Health Science, Vol. 16, No. 2, pp. 66-72, 2013).

The muscle supporter 100 of the second embodiment improves the blood flow and lymph circulation in a muscle to be trained and a region surrounding the muscle. The muscle supporter 100 not only strengthens the muscles but also improves the blood flow and lymph circulation.

The sheet device 200 in the muscle supporter 100 is thin and elastic. For this reason, the muscle supporter 100 is worn at the same sense of use as the related art muscle supporter. The sheet device 200 is not so conspicuous. Other examples of muscle strength condition The muscle supporter 100 may acquire the muscle strength condition of each muscle based on information other than the muscle potential.

The muscle supporter 100 detects the muscle strength condition in response to a change in the blood flow in the muscle when the muscle is stimulated. The muscle strength condition is information about a difference in the blood flow between the muscle with a predetermined EMS current flowing therethrough and the muscle with no current flowing therethrough. The muscle strength condition detector 410 includes an EMS electrode pair to stimulate the muscle and a blood flow sensor to measure the blood flow through the muscle. The movement controller 320 compares a rate of increase in the blood flow value with the muscle under predetermined muscle stimulation with a threshold value predetermined according to sex and age. The movement controller 320 determines a muscle having a rate of increase in the blood flow value less than the threshold value as the support target muscle.

A muscle weak in strength does not contract so much in response to stimulation by EMS, and the blood flow does not increase so much either. The blood flow value greatly decreases with age, and also varies greatly from person to person. Whether to perform the assist movement is appropriately determined by paying attention to the rate of increase in the blood flow value.

The blood flow sensor described in Takanori KIYOKURA, Shinji MINO, and Junichi SHIMADA "Continuously carried compact laser Doppler blood flow meter" Nippon Telegraph and Telephone Corporation (NTT) Technical Review, pp. 25-27, Nov. 2005 may be used for the blood flow sensor in the second embodiment. The blood flow sensor includes a laser diode and a phototransistor. The organic laser diode described in Japanese Unexamined Patent Application Publication No. 2009-48837 may be used for the laser diode of the blood flow sensor. The organic phototransistor manufactured of a polymer based thin-film transistor and described in Japanese Unexamined Patent Application Publication No. 2007-300112 may be used for the phototransistor of the blood flow sensor.

The EMS electrode pair used to acquire the muscle strength condition may be common to the EMS electrode pair 230 used to support the muscle.

Another Acquisition Method of Muscle Contraction Timing

The muscle supporter 100 may acquire the muscle contraction timing from information other than the muscle potential.

The muscle supporter 100 may acquire the muscle contraction timing of each muscle based on a potential between two points on the skin covering the muscle. The muscle contraction timing detector 420 includes a piezoelectric element that detects a potential between the two points on the skin. If the muscle contracts or relaxes, the distance between the two points on the skin also changes, generating an electromotive force in the piezoelectric element. The movement controller 320 detects the muscle contraction start timing and the muscle relaxation start timing of the corresponding muscle based on the electromotive force of each piezoelectric element.

The piezoelectric element described in International Publication No. 2012/137897 may be used for the piezoelectric element that detects a change in the distance between the two points on the skin.

Modifications

The muscle supporter 100 may perform the detection mode operation prior to each support mode operation.

The muscle supporter 100 may be worn on the upper half body, the arm, the hip, or the legs, and other parts of the body. The blocks that acquire the muscle strength condition and the muscle contraction timing and performs the assist movement, and the sensor and the movement element in each block are laid out at locations corresponding to the muscles.

Some or all functions of the controller 300 may be implemented in another apparatus, having another function as a main function, such as a cellular phone.

The above-described functions may be implemented in a server over a network. More specifically, some functions of the muscle supporter 100 may be implemented in cloud computing. In such a case, the movement controller 320 includes at least a communication unit, and transmits, to the server, information indicating the muscle strength condition and information indicating the muscle contraction timing, and then acquires a target for the muscle support and the muscle support timing.

The muscle supporter 100 may include the movement controller 320 that is arranged on each block to perform the operation for that block.

A muscle supporter of the disclosure includes a sheet attachable to skin covering a muscle, a muscle strength condition detector that is disposed on the sheet member and detects information related to muscle strength condition of the muscle, a muscle contraction timing detector that is disposed on the sheet member and that, in operation, detects a muscle contraction timing of the muscle, and a muscle assist movement provider that is disposed on the sheet member and that, in operation, assists the muscle to contract in response to the detected information and the detected muscle contraction timing.

In the muscle supporter, the muscle contraction timing detector may detect as the muscle contraction timing at least a portion of a period extending from a timing when the muscle starts contracting to a timing when the muscle starts relaxing.

The muscle supporter may further include a movement controller that, in operation, causes the muscle assist movement provider to assist the muscle on condition that a level of a muscle strength indicated as the muscle strength condition is lower than a threshold value, and that the muscle is at the muscle contraction timing.

The muscle supporter may further include a movement controller that, in operation, switches between a detection mode and a support mode, cause the muscle strength condition detector to operate in the detection mode, and cause the muscle contraction timing detector and the muscle assist movement provider to operate in the support mode.

In the muscle supporter, the muscle assist movement provider may include an electrical muscle stimulation electrode pair that causes an electrical muscle stimulation current to flow through the muscle on condition that a level of a muscle strength indicated as the muscle strength condition is lower a threshold value.

In the muscle supporter, the muscle strength condition detector may include a muscle potential sensor that detects a muscle potential of the muscle. The muscle strength condition detector may detect, as the information related to the muscle strength condition, at least information related to a low-frequency component ratio of time data of the muscle potential.

In the muscle supporter, the muscle strength condition detector may include an electrical muscle stimulation electrode pair that causes a predetermined electrical muscle stimulation current to flow through the muscle, and a blood flow sensor that measures a blood flow value in the muscle. The muscle strength condition detector detects, as the information related to the muscle strength condition, at least information related to a difference between the blood flow value with the predetermined electrical muscle stimulation current flowing and the blood flow value with the predetermined electrical muscle stimulation current not flowing.

In the muscle supporter, the muscle contraction timing detector may include a muscle potential sensor that detects a muscle potential of the muscle. The muscle contraction timing detector detects as the muscle contraction timing a timing when a value of the muscle potential of the muscle satisfies a predetermined condition.

In the muscle supporter, the muscle contraction timing detector may include a piezoelectric element pair that measures a distance between predetermined two points on the skin. The muscle contraction timing detector detects as the muscle contraction timing a timing when a change in the distance satisfies a predetermined condition.

In the muscle supporter, the sheet member may be attachable to the skin covering a plurality of predetermined muscles. The muscle strength condition detector detects the information related to the muscle strength condition of each of the plurality of predetermined muscles. The muscle contraction timing detector detects the muscle contraction timing of each of the plurality of predetermined muscles. The muscle assist movement provider assists movement on each of the plurality of predetermined muscles in response to the muscle strength condition and the muscle contraction timing of each of the plurality of predetermined muscles.

In the muscle supporter, the sheet member may include at least part of a texture member that is elastic and is worn at a predetermined location of a body of a user to assist the muscle to contract.

The disclosure is related to a muscle support method. The muscle support method includes detecting information related to muscle strength condition of a muscle by using a detector disposed on a sheet member attachable to skin covering the muscle, detecting a muscle contraction timing of the muscle by using the detector, and assisting the muscle to contract in response to the detected information and the detected muscle contraction timing by using a movement element disposed on the sheet member.

The disclosure provides the muscle supporter that effectively performs the muscle support and the muscle support method of the muscle supporter.

What is claimed is:

1. A muscle support method, comprising:
    detecting, in a detection mode, a first muscle potential of a first muscle, with a first muscle potential sensor in a sheet member attachable to skin covering the first muscle;
    calculating, in the detection mode, a first low-frequency component ratio comprising a ratio of an integral value of a low-frequency component of the first muscle potential to an integral value of an entire bandwidth component of the first muscle potential;
    determining, in the detection mode, whether the first muscle is to be supported, based on the first low-frequency component ratio;
    detecting, in a support mode, immediately after the detection mode, a second muscle potential of the first muscle;
    causing a first current, in the support mode, at a start time, between a first electrical muscle stimulation electrode pair in the sheet member and through the first muscle, if the first muscle is to be supported, the start time being determined based on the second muscle potential; and
    stopping the first current in the support mode, at a second time, the second time being determined based on an average potential of the first muscle detected by the first muscle potential sensor.

2. A muscle support method according to the claim 1, further comprising:
    detecting, in the detection mode, a third muscle potential of a second muscle, using a second muscle potential sensor in the sheet member, the skin covering the second muscle;
    calculating, in the detection mode, a second low-frequency component ratio, that is a ratio of an integral value of a low-frequency component of the third muscle potential to an integral value of an entire bandwidth component of the third muscle potential; and
    determining, in the detection mode, whether the second muscle is to be supported, based on the second low-frequency component ratio,
    wherein no current flows through the second muscle between one or more electrical muscle stimulation electrode pairs in the sheet member in the support mode if the second muscle is not to be supported.

3. A muscle supporter, comprising:
    a first muscle potential sensor in a sheet member attachable to skin covering a first muscle that is configured to detect a first muscle potential of the first muscle in a detection mode and detect a second muscle potential of the first muscle in a support mode, the support mode being performed immediately after the detection mode;
    a controller configured to calculate a first low-frequency component ratio, in the detection mode, that is a ratio of an integral value of a low-frequency component of the first muscle potential to an integral value of an entire bandwidth component of the first muscle potential, and configured to determine whether the first muscle is to be supported, in the detection mode, based on the first low-frequency component ratio; and
    a first electrical muscle stimulation electrode pair in the sheet member that causes a first current, in the support mode, at a start time, through the first muscle if the first muscle is to be supported, the start time being determined based on the second muscle potential, and that stops the first current in the support mode, at a second time, the second time being determined based on an average potential of the first muscle detected by the first muscle potential sensor.

4. A muscle supporter according to the claim 3, further comprising:
    a second muscle potential sensor in the sheet member configured to detect a third muscle potential of an second muscle, in the detection mode, the skin covering the second muscle,
    wherein the controller is configured to calculate a second low-frequency component ratio, in the detection mode, that is a ratio of an integral value of a low-frequency component of the third muscle potential to an integral value of an entire bandwidth component of the third muscle potential,
    wherein the controller is configured to determine whether the second muscle is to be supported, in the detection mode, based on the second low-frequency component ratio, and
    wherein no current flows through the second muscle between one or more electrical muscle stimulation electrode pairs in the sheet member in the support mode if the second muscle is not to be supported.

* * * * *